(12) United States Patent
Ahvenainen et al.

(10) Patent No.: US 6,325,974 B1
(45) Date of Patent: Dec. 4, 2001

(54) PACKAGE FOR DECAYABLE FOODSTUFFS (75) Inventors: Raija Ahvenainen; Timo Pullinen; Eero Hurme; Maria Smolander; Matti Siika-Aho, all of Espoo (FI)

(73) Assignee: Valtion Teknillinen Tutkimuskeskus

( * ) Notice: Subject to any disclaimer, the term of this patent is extended or adjusted under 35 U.S.C. 154(b) by 0 days.

(21) Appl. No.: 09/297,792

(22) PCT Filed: Nov. 7, 1997

(86) PCT No.: PCT/FI97/00680

§ 371 Date: May 6, 1999

§ 102(e) Date: May 6, 1999

(87) PCT Pub. No.: WO98/21120

PCT Pub. Date: May 22, 1998

(30) Foreign Application Priority Data

Nov. 8, 1996 (FI) .......................................... 964508

(51) Int. Cl.[7] .............................. B65D 79/02; G01N 21/00
(52) U.S. Cl. .................................. 422/58; 422/61; 436/1; 436/164; 426/232; 116/206
(58) Field of Search ........................... 422/58, 61; 436/1, 436/164; 426/232; 116/206

(56) References Cited

U.S. PATENT DOCUMENTS

| 2,485,566 | * 10/1949 | Clark ........................................... 43/2 |
| 3,067,015 | * 12/1962 | Lawdermilt ................................ 436/2 |
| 3,768,976 | 10/1973 | Hu et al. . |
| 4,003,709 | 1/1977 | Eaton et al. . |
| 4,772,707 | 9/1988 | Hamon et al. . |
| 5,053,339 | * 10/1991 | Patel ........................................ 436/2 |
| 5,228,573 | 7/1993 | Pavelle et al. . |
| 5,306,466 | 4/1994 | Goldsmith . |

FOREIGN PATENT DOCUMENTS

| 0629497 | 12/1994 | (EP) . |
| 94802 | 7/1995 | (FI) . |

OTHER PUBLICATIONS

Japanese Patent Abstract JP 55041875 dated Mar. 24, 1980.
Japanese Patent Abstract 62–259059 dated Nov. 11, 1987.
Japanese Patent Abstract 61–152299 dated Jul. 10, 1986.

* cited by examiner

Primary Examiner—Lyle A. Alexander
(74) Attorney, Agent, or Firm—Andrus, Sceales, Starke & Sawall, LLP (57) ABSTRACT

Package (1) for decayable foodstuffs (2), consisting of a package material (3) and forming a mainly closed package space (4) and a mainly closed indicator space (5) for an indicator (6). The indicator space (5) forms an exterior wall (8) adjoining the environment (7) and made of a material (9) with a controllable gas permeability so that gas can penetrate through the exterior wall into the indicator space in a controlled manner as the package 91) is aging, so that the indicator (6) will indicate the entry of gas into the indicator space and therefore the aging of the package upon the lapse of a certain time after the package was exposed to the environment; and an interior wall (10) of the indicator space (10), adjoining the package space 94) and made of a material controllably permeable to gas so that gas entering into and/or generated in the package space can penetrate from the package space into the indicator space in a controlled manner and the indicator will indicate that gas has entered into the package space.

23 Claims, 10 Drawing Sheets

PACKAGE FOR DECAYABLE FOODSTUFFS

BACKGROUND OF THE INVENTION

The present invention relates to a package for decayable foodstuffs, which package consists of a package material and forms a mainly closed package space and a mainly closed indicator space for an oxidation indicator.

Specification EP 0627,363 presents a foodstuff package containing an indicator that changes its colour when the concentration of gas inside the package reaches a predetermined level. The indicator may consist of a label or printed material formed on the surface of the package. The indicator may be separated by a gas-permeable foil from the product contained in the package. The indicator may be a carbon dioxide or oxygen indicator. However, such an indicator only responds to gas penetrating into the package or gas formed inside the package. The indicator does not respond to ageing of the packge and/or to a rise in the temperature of the package.

Specification EP 0629497 presents a package material that comprises two foils joined together and forming between them a space for a colour indicator. When the package material is damaged, the colour indicator reacts with the gas entering into the package and changes its colour. However, such a leakage indicator only responds when the package material is damaged, it does not respond to decay of the foodstuff in itself.

Specifications U.S. Pat. No. 4,772,707, JP 55-41875, JP 61-152299, JP 62-259059 and FI 94802 present various absorbents for absorbing the oxygen remaining in the package, stabilisers, such as reducing agents, for stabilising a colorant before the foodstuff is packaged, and colorants for indication of gas penetrating into the package e.g. via a leakage or decay of the foodstuff. The indicators proposed in these specifications are placed in the package in conjunction with the packaging of the foodstuff; in other words, the indicators are separate from the package and they are manufactured separately. The manufacture and especially the storage of this kind of separate indicators before they are placed in a package is difficult as the indicators tend to react with oxygen as soon as they come into contact with ambient air. Further difficulties arise from the separate manufacture, storage and handling of the indicators.

Generally, the specifications referred to above relate to various leakage indicators designed for use in foodstuff packages and indicators that respond to damage of the package and decay in itself. However, the specifications referred to do not describe an indicator or package that would respond to ageing of the package and/or to an excessive rise in the temperature of the package and to the volatile compounds produced as a result of decay of the foodstuff.

SUMMARY OF THE INVENTION

The object of the present invention is to eliminate the drawbacks described above.

A specific object of the invention is to present a new type of active and intelligent package for decayable foodstuffs, which package contains an indicator, preferably an oxidation indicator, that makes it possible to detect a leakage in the package, incipient decay of the foodstuff or other chemical change and especially ageing and/or undesirable high temperature or thermal load.

A further object of the invention is to present a new type of package and indicator that reacts to volatile compounds produced as a result of decay of the foodstuff.

A further object of the invention is to present a new type of package for decayable foodstuffs that allows easier, simpler and more rationalised packaging of foodstuffs and especially placement of a freshness indicator in the package.

A specific object of the present invention is to produce a new type of package for foodstuffs that allows a separate indicator to be placed on the package before, during or after the packaging of the foodstuff.

A further object of the invention is to present a new type of package for foodstuffs that allows an indicator to be placed in the package independently of the time of packaging.

As for the features characteristic of the present invention, reference is made to the claims.

The invention is based on research work during which a new type of package was developed so that ageing and undesirable high temperature or thermal load of the package as well as decay can be recognised from an indicator comprised in the package.

In the package of the invention, an indicator space, e.g. an oxidation indicator space, forms an external wall adjoining the environment, which wall is made of a material controllably permeable to an atmospheric gas, preferably oxygen, permitting controlled entry of gas through the external wall into the indicator space as the package is ageing. The indicator indicates that gas has penetrated into the indicator space, thus showing the ageing of the package upon the lapse of a certain length of time after the package was exposed to the environment and especially to atmospheric oxygen.

Correspondingly, the interior wall between the indicator space and the package space can be made of a material with a controllable, preferably good gas permeability, so that oxygen or other gases leaking into the package space and/or generated in it, e.g. compounds produced via decay of the foodstuff, can penetrate from the package space into the indicator space, with the result that the indicator will indicate the penetration of oxygen or other gases into the indicator space. The interior wall of the indicator space can also be made of a material having a temperature-dependent gas permeability.

The exterior wall of the indicator space may be made of any known material permeable to gas, especially oxygen, such as polyethylene, polypropylene, other polyolefin, polyamide or in general any other plastic material commonly used as package material. The exterior wall may also be made of a cellulose based material, such as surface-treated paper, cardboard, dissolving-pulp based foil material or other cellulose or polyacetate based material. Further, the exterior wall of the indicator space may be made of a laminate of the above-mentioned or other known package materials or some other kind of material combination.

The gas permeability of the exterior wall of the indicator space may be based on the thickness of the wall material, its general structural permeability or porosity or its artificial micro-perforation. The overall gas permeability is also based on the area of the exterior wall of the indicator space. Generally, the permeability of the wall material is so adjusted that it corresponds to the length of time the indicator is intended to indicate. In packages designed for a shorter indication time, a thinner wall material, a more porous wall material structure, a larger area of micro-perforations and/or a larger gas permeable-external wall area and/or some other means for increasing permeability is used. Correspondingly, in packages designed for a longer ageing time, a thicker wall material, a less porous wall material structure or a structure with fewer perforations and/or a smaller exterior wall area or some other known means is used to reduce the permeability of the exterior wall.

The indicator can be adjusted to indicate the desired ageing of the package by selecting the wall material, or its permeability, i.e. its thickness, porosity, size of microperforation, external wall area and/or a combination of these, so that it corresponds to the desired package ageing time to be indicated. Further, the indication of ageing of the package, i.e. the response of the indicator, can be influenced by selecting the indicator according to the desired ageing time, in other words, it is possible to use an indicator with a faster or a slower response. Further, the indication of ageing of the package can be influenced by using a combination of an indicator and a gas absorbent and/or other stabiliser that absorbs a predetermined amount of gas, which consists of the residual gas remaining in the package or gas that otherwise penetrates into the indicator space.

In a preferred embodiment of the present invention, the indicator space wall adjoining the environment is made of a material whose permeability to oxygen depends on temperature, so that the entry of oxygen into the indicator space is temperature-dependent and the package ageing indication given by the oxidation indicator is dependent on temperature. Thus, the temperature-dependent wall material may be e.g. one of the above-mentioned wall materials whose permeability increases as the temperature rises; correspondingly, it is also possible to use a wall material whose permeability decreases as the temperature rises. Accordingly, when it is to be indicated that the package has been exposed to a high thermal load, a wall material whose permeability increases with temperature is used, i.e. at a high temperature more oxygen can penetrate into the package.

The exterior wall of the indicator space is preferably at least partially made of a substantially transparent material to allow easy observation of a colour change of the colorant.

If desired, the exterior indicator space wall adjoining the environment can be provided with a protector substantially impermeable to gas, which can be removed e.g. during packaging or when the package is moved e.g. from the cold storage room of a shop to a shop counter. The protector may consist of e.g. a removable plastic foil, sticker tape, i.e. generally a removable protector that covers at least the exterior indicator space wall adjoining the environment or, if desirable, a protector covering most of the package. By means of the protector, the beginning of ageing of the package can be adjusted as desired.

If desirable, the package material may form a laminate with the indicator space wall material. The indicator can also be laminated in the package material.

Other than laminating, the indicator can also be attached to the package material by gluing, by means of a sticker joint or in general by any fastening method known in packaging technology. Further, the package material may have only a limited perforated area and the indicator may be attached to the outside of the package over the perforated area.

In an embodiment of the invention, the package material of the foodstuff package comprises a penetrable spot permeable to a factor indicating decay of the foodstuff. Likewise, the indicator comprises a corresponding penetrable spot permeable to a factor indicating decay of the foodstuff. The indicator must be attached onto the foodstuff package so that the penetrable spots lie opposite to each other.

In an embodiment of the invention, the package material exterior surface surrounding the penetrable spot on the foodstuff package and/or the exterior indicator surface surrounding the penetrable spot on the indicator are/is provided with a protector or protectors, which are removed when the indicator is attached to the package.

In a preferred embodiment, the area permeable to a factor indicating decay of the foodstuff on the foodstuff package and/or on the indicator has been formed by perforating. Correspondingly, the penetrable spot on the package and/or indicator may be made of a material controllably permeable to a factor indicating decay of the foodstuff, e.g. to gas, so that oxygen or other gases, e.g. other compounds formed as a result of decay of the foodstuff, entering into the package space through a leakage and/or generated in it can penetrate from the package space into the indicator space, so that the indicator will indicate that oxygen or other gases have penetrated into the indicator space.

Further, according to the invention, the foodstuff package and/or indicator space may be provided with a perforating element, e.g. a sharp element so that when the indicator is attached to the package or to the package material, the perforating element will make a hole, a perforation or an equivalent penetrable spot in the indicator and/or package material.

In an embodiment of the invention, the indicator is preferably fabricated separately and attached onto the penetrable spot on the exterior surface of the foodstuff package e.g. before, during or after the packaging.

The foil on the inside of a separately fabricated indicator and/or the penetrable spot in the package material of the foodstuff package may be provided with a protector impenetrable to gas, the protector being removed when the indicator is attached to the package. In this case the indicator can be attached to the package at any time.

The package may preferably comprise one or more freshness indicators responsive to various changes in conditions, such as gas concentrations, temperature changes and/or temperature-time dependence or to any kind of change in conditions indicative of decay of the foodstuff. The freshness indicators and/or other indicators used may be any kind of indicators known in the art, e.g. from the specifications referred to in the preamble to the present description.

The indicator may be any type of indicator that changes its colour when exposed to an atmospheric gas, e.g. oxygen, and/or a volatile compound produced as a result of decay of the foodstuff contained in the package. The colour change may occur either directly or indirectly, e.g. via a triggering mechanism suitably selected. The indicator or indicator system may comprise both colour change mechanisms based on direct effect and colour change mechanisms based on indirect effect.

The indicator used may have several functions, in other words, it may respond to more than one change in conditions. In a preferred embodiment, the indicator is an oxygen indicator. It responds to oxygen entering from outside the package, indicating the ageing or thermal load of the package. The oxygen indicator also responds to oxygen entering the package through a leak. Furthermore, the oxygen indicator can function via an indirect mechanism as a decay indicator. In this case, the volatile compounds generated as a result of decay penetrate into the indicator space and, by the agency of a suitably selected catalyst, e.g. an enzyme, or a pH change, can produce a colour change in the indicator.

Thus, for example, the indicator used may consist of a colouring agent sensitive to oxygen and/or to a compound generated via decay and/or to a pH change and/or of an enzyme that uses oxygen or a compound produced through decay as its cosubstrate/substrate. Examples of redox colour indicators that can be used are methylene blue, gallocyanine, methylene red, anthraquinones, safranine, beta carotene, lycopene, resorufin, thionin, cresyl blue, toluidine blue and janus green. Examples of other foodstuff colouring agents capable of reacting to environmental changes are anthocyanins, precipitated indigo, patent blue V, amaranth, carmosine, paraorange and erythrocine. Examples of suitable enzymes are alcohol oxidase, aryl-alcohol oxidase, secondary alcohol oxidase, aldehyde oxidase, sulphite oxidase, thiol oxidase, catechol oxidase, laccase and glucose oxidase. Examples of pH-sensitive colouring agents are methyl orange, methyl red, lacmus, bromthymol blue and carminic acid.

If necessary, the indicator may also contain a substrate, a reducing agent and/or an oxygen absorbent. As for the substrates, primarily when enzymes are used, a substrate typical of each enzyme can be used. Examples of usable reducing agents are e.g. carbohydrates, such as reductible sugars, e.g. glucose and fructose, and zinc. Examples of possible oxygen absorbents are those described in Finnish patent FI 94802.

Moreover, the indicators may contain various extenders, so-called basic components, such as sodium hydroxide, sodium carbonate, sodium hydrogen carbonate, sodium silicate. Further, the indicator may comprise liquids, e.g. water, ethanol. The indicator may further contain extenders such as kaolin, silicon oxide, talcum, etc.

BRIEF DESCRIPTION OF THE SEVERAL VIEWS OF THE DRAWINGS

In the following, the invention will be described in detail by the aid of an embodiment example by referring to the attached drawings, in which.

DETAIL DESCRIPTION OF THE INVENTION

Figure 1:
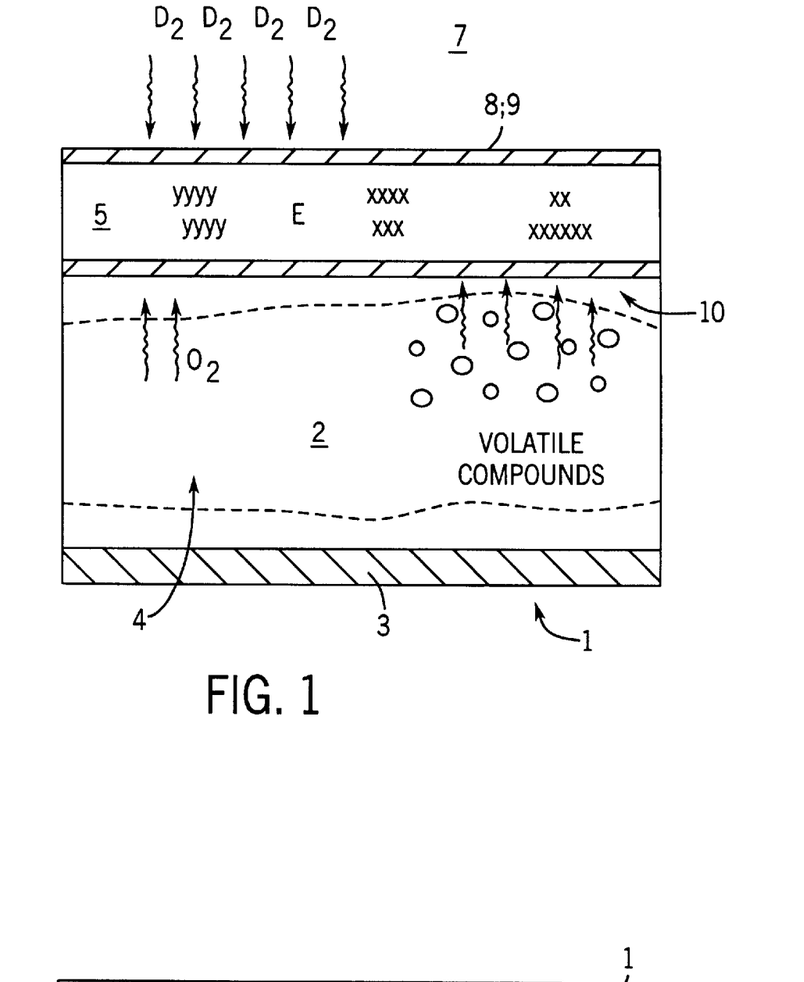
FIG. 1 presents a diagram representing a package according to the invention.

FIG. 1 shows part of a package 1 with a decayable foodstuff 2 packed in it. The package consists of a package material 3 having a low permeability or no permeability to oxygen and forms a mainly closed package space 4, in which the foodstuff 2 is placed, and a mainly closed oxidation indicator space 5 with an oxidation indicator 6 placed in it. According to the invention, the oxidation indicator space 5 forms an external wall 8 adjoining the environment 7, made of a material 9 with controllable permeability to oxygen. Thus, oxygen can penetrate into the oxidation indicator space in a controlled manner as the package is ageing, and the oxidation indicator reveals the entry of oxygen into the oxidation indicator space and therefore the ageing of the package upon the lapse of a certain time after the package was exposed to the environment.

Therefore, the consumer can immediately see from the indicator how long the package has been subject to environmental influence, e.g. on a shelf in a shop, or the exact time of packaging.

In the embodiment presented in FIG. 1, the exterior wall 8 of the oxidation indicator space 5 is made of a material 9 having a temperature-dependent permeability to oxygen, so that the entry of oxygen into the oxidation indicator space is temperature-dependent and the oxidation indicator also gives a temperature-dependent indication of ageing of the package. In the embodiment presented, the active layer of the indicator 6 contains an oxidative enzyme E, which has an effect only if oxygen is present, and a substrate Y for the enzyme. The enzyme E and the substrate Y are so selected that the oxidation product emerging in an enzymatic reaction is a typical volatile compound X produced in mould-induced decay. Thus, the compound X can be generated inside the package when the foodstuff 2 contracts mould, in which case the compound X can penetrate into the oxidation indicator space 5 through the indicator space interior wall 10 adjoining the package space 4. Further, if the package leaks, oxygen will enter into the package and the oxygen can penetrate into the indicator space 5 through its interior wall 10 adjoining the package space 4; in other words, the interior wall 10 is made of a material permeable to oxygen and the volatile compound X produced in mould-induced decay. In this case, the oxidation indicator 6 will reveal oxygen penetrating through the wall 8 from outside the package, volatile compounds X generated inside the package via moulding of the foodstuff 4 and penetrating through the interior wall 10, and/or oxygen penetrating from inside the package in consequence of a breakage in the package. Therefore, the oxidation indicator effectively reveals package ageing, foodstuff decay and/or a damaged package.

The versatile oxidation indicator described above is expressly based on the structure of the exterior wall 8 of the oxidation indicator 6 and its interior wall 10 adjoining the package space 4, the latter wall having a good permeability to oxygen and compounds produced in decay of the foodstuff 2 so that the indicator will quickly respond to said compounds.

Figure 2:
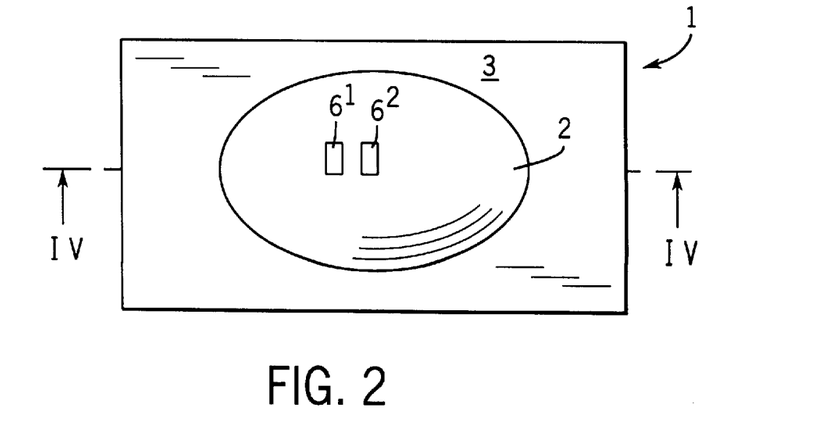
FIG. 2 presents another package according to the invention.
Figure 3:
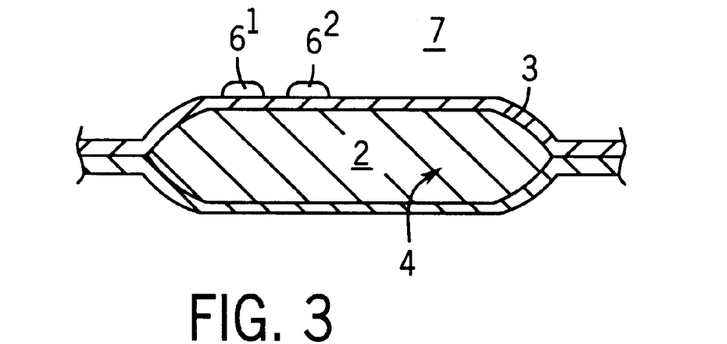
FIG. 3 presents a section taken along line IV—IV in FIG. 2.

FIGS. 2 and 3 show another package 1 according to the invention, which in principle corresponds to the package presented in FIG. 1. The package in FIGS. 2 and 3 comprises two freshness indicators $6^1$, $6^2$ containing one or more colorants 13 responsive to a factor indicating decay of the foodstuff, a stabiliser 14, such as a reducing agent or other stabilising agent for stabilising the colorant before and during packaging of the foodstuff, and a gas absorbent 15 for binding the gas that penetrates into the package before and during packaging on the foodstuff and reacts with the colorant. According to the invention, the freshness indicators $6^1$, $6^2$ are permanently incorporated in the package. Freshness indicator $6^1$ responds to penetration of oxygen into the package and freshness indicator $6^2$ responds when the temperature exceeds a given temperature limit.

The freshness indicators $6^1$, $6^2$, their colorant, stabiliser and gas absorbent are known in themselves and will not be described here in detail.

Figure 4:
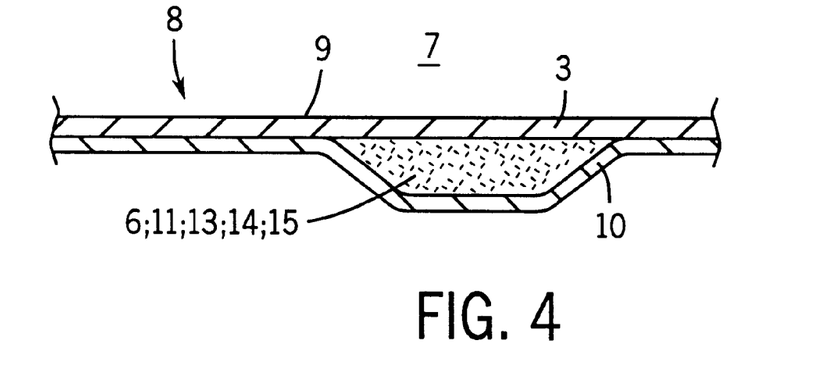
FIG. 4 presents a magnified section of the package material in FIGS. 2 and 3.

FIGS. 3 and 4 illustrate the permanent placement of the freshness indicators 6 in the package, i.e. in the package material 3. The freshness indicator 6 together with its component agents 13–15 are laminated between the package materials forming the outer layer 8 and inner layer 10 of the package so that the package material and the freshness indicator form a laminate. The exterior wall 8 has a controllable permeability to oxygen, the interior wall 10 has a good permeability to oxygen and other gases reactive with the colorant 13 and is impermeable to water.

The package structure developed allows a gas, e.g. oxygen, reactive with the colorant to penetrate through the interior wall 10 permeable to oxygen into the leakage indicator 6 from inside the package and also from outside the package through the exterior wall 8 with a controllable permeability to oxygen. The residual oxygen remaining in the package is absorbed into the gas absorbent 15 contained in the leakage indicator and therefore does not cause a colour change in the colorant. The stabiliser 14, i.e. reducing agent, keeps the colorant in a reduced state during packaging. Only a larger amount of oxygen penetrating into the indicator 6 comprised in the package will cause a colour change in the colorant, which can be seen from outside the package through a transparent spot in the package.

Figure 5:
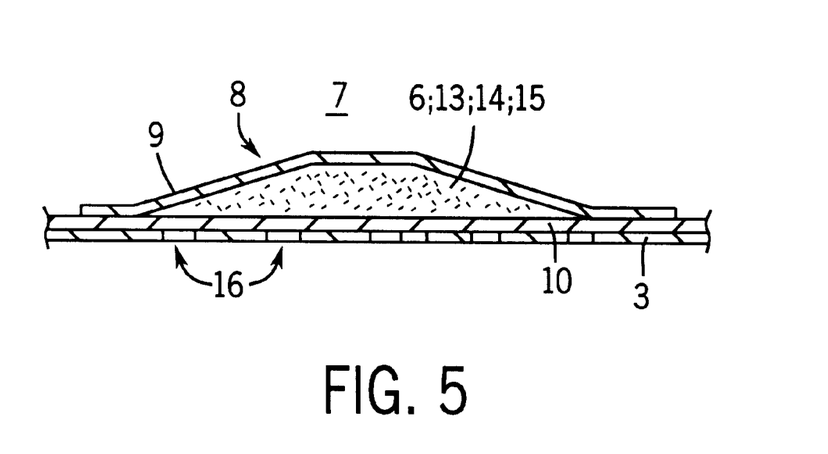
FIG. 5 presents a section through package material according to another embodiment of the invention.

In the embodiment presented in FIG. 5, the package material 3 has been perforated 16, e.g. in conjunction with the manufacture of the foil or during packaging. Attached with a sticker joint to the perforated area on the outside of the package is a freshness indicator 6, whose exterior wall 8 is controllably permeable to oxygen, and the interior wall glued onto the perforated area is permeable to oxygen and a gas reactive with the colorant. The leakage indicator in FIG. 6 functions in the same way as the leakage indicator in FIGS. 3–5.

Figure 6:
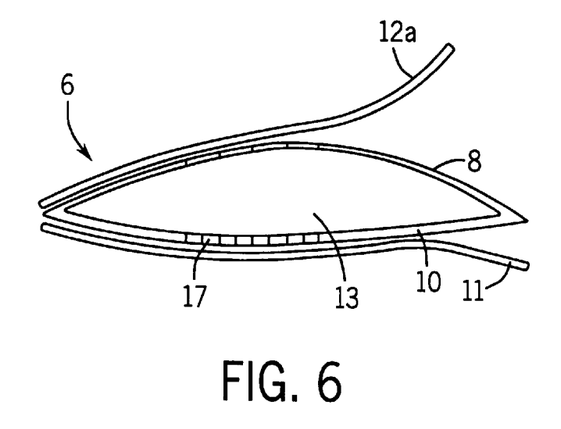
FIG. 6 presents an indicator according to the invention in lateral sectioned view.
Figure 7:
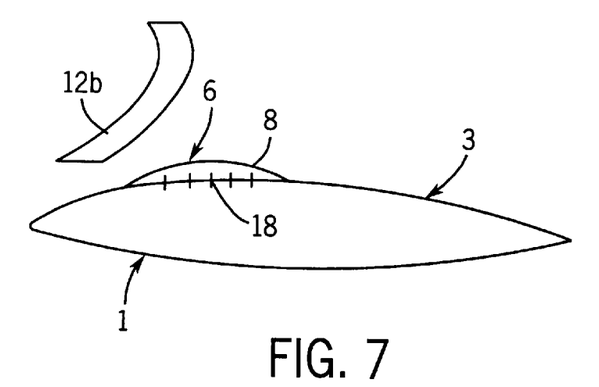
FIG. 7 presents a third foodstuff package according to the invention, with an indicator as presented in FIG. 6 attached to it.

FIGS. 6–7 show a leakage indicator 6 for a foodstuff package 1. The indicator 6 is intended to be attached onto the foodstuff package 1 as shown in FIG. 7.

The indicator 6 consists of an exterior wall 8 and an interior wall 10 forming between them a closed indicator space 5, in which the colorant 13 and other chemicals needed, such as a stabiliser and a gas absorbent, are placed. The components can also be placed in separate compartments that may be provided inside the indicator space.

The indicator 6 is intended to be attached onto the foodstuff package. The indicator 6, in the present embodiment its interior wall 10, is provided with a penetrable spot 17 permeable to a factor indicating decay of the foodstuff. Correspondingly, the package material of the foodstuff package 1 comprises a penetrable spot 18 permeable to a factor indicating decay of the foodstuff. The indicator 6 must be attached onto the foodstuff package with the penetrable spots 17, 18 placed opposite to each other.

In the embodiment presented, both the penetrable spot 17 of the indicator and the penetrable spot 18 of the foodstuff package are made of gas-permeable material, e.g. thin polyethylene, polypropylene or the like, permeable to the factor indicating decay of the foodstuff. Alternatively, the penetrable spot may also be a perforated area. Further, in the embodiment persent, the penetrable spots are covered with a protector 11, 12b impenetrable to gas, e.g. a plastic foil, removable sticker tape or the like, which is removed from the penetrable spot when the indicator is to be attached to the foodstuff package, with the penetrable spots facing each other; in FIG. 7 the protector 12b has been removed. The area surrounding the penetrable spot 17 in the exterior wall 10 of the indicator in the embodiment presented can be provided with sticker adhesive to allow gas tight attachment of the indicator onto the foodstuff package. Similarly, the area surrounding the penetrable spot 18 on the foodstuff package 1 can be provided with sticker adhesive to attach the indicator onto the foodstuff package. Instead of sticker attachment, it is possible to use any known method of attachment, such as gluing, lamination, etc.

The exterior wall 8 of the indicator 6 may be made of a material impermeable to gas. However, in the embodiment presented, the external wall 8 is made of a material controllably permeable to oxygen and/or carbon dioxide, i.e. a gas that reacts with the colorant of the indicator, such as e.g. thin polyethylene, polypropylene or the like. The external wall 8 is also provided with a protector 12a to allow the indicator to be exposed to the environment e.g. when it is attached onto the foodstuff package.

Figure 8:
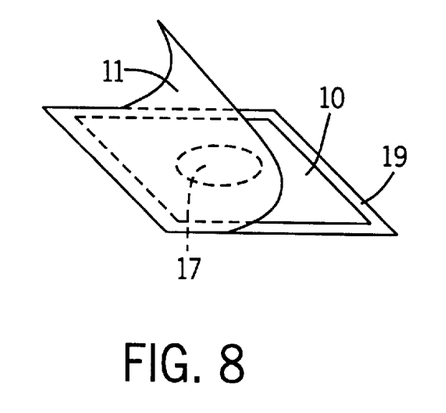
FIG. 8 presents a perspective view of another indicator according to the invention.

In the embodiment presented in FIG. 8, the area surrounding the penetrable spot 17 in the interior wall 10 of the indicator 6, i.e. the part to be placed against the penetrable spot 18 on the foodstuff package 1, is provided with an adhesive surface 19. The protector 11 of the interior wall 10 is made of plastic material impermeable to oxygen, e.g. polyethylene; in the figure, the protector has been partially torn off to permit the indicator to be glued onto the foodstuff package.

EXAMPLE 1

Reaction between Myoglobin and Hydrogen Sulphide

A solution of myoglobin (0.4 mg/ml) prepared in a sodium phosphate buffer (40 mM, pH 6.8) was divided into 2 ml portions and enclosed in 22-ml gas chromatographic bottles. A known amount of gaseous hydrogen sulphide was injected into the bottles. The myoglobin bottles were incubated at +4° C. for 24 hours. Then the bottles were opened and the absorption spectra for the myoglobin solutions in the visible light wavelength range were measured. The measurement and hydrogen sulphide addition were repeated upon the lapse of 2, 6, 8 and 13 days after the experiment was started. The experiment was repeated as follows. The myoglobin solution was nitrified before closing the chromatographic bottle, and after the bottle was closed the head space of the bottle was also nitrified before the addition of hydrogen sulphide and the spectra were recorded after 24 hours from the beginning of the experiment.

Figure 9:
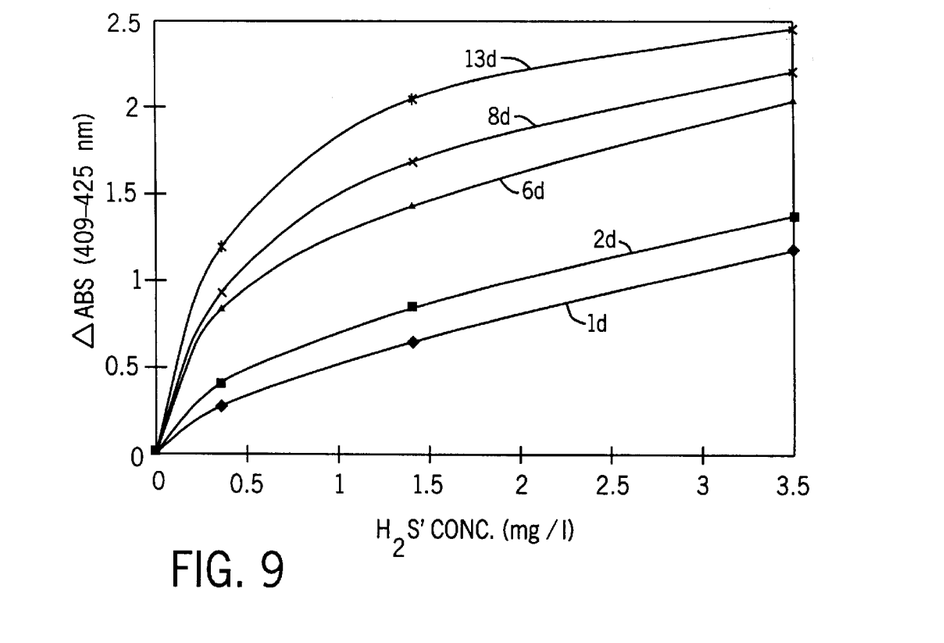
FIG. 9 illustrates the change in the absorption peak in the wavelength range of 409–425 nm for soluble myoglobin as compared with a blank sample ($[H_2O]=0$) as a function of hydrogen sulphide concentration (non-nitrified solution)
Figure 10:
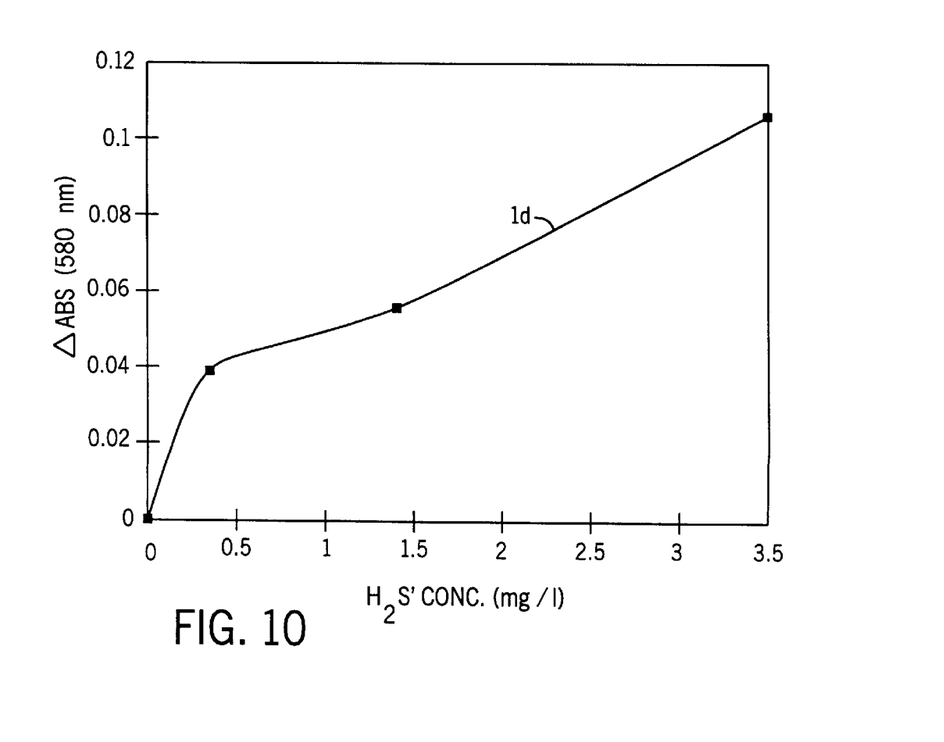
FIG. 10 illustrates the change in absorption (580 nm) of soluble myoglobin as compared with a blank sample ($[H_2O]=0$) as a function of hydrogen sulphide concentration (nitrified solution)

It was noticed that the colour of the myoglobin solution was changed from brownish red to a greenish colour by the action of hydrogen sulphide. The colour change betame more pronounced as the concentration of hydrogen sulphide was increased. Several changes took place in the spectrum of myoglobin due to the hydrogen sulphide. FIG. 9 shows the change in the absorption peak in the wavelength range of 409–425 nm as function of hydrogen sulphide concentration at different times of measurement (non-nitrified solution). It can be seen that the change in the absorption peak is dependent on both the hydrogen sulphide concentration and the length of time during which the myoglobin solution is in contact with hydrogen sulphide. In nitrified myoglobin solution, the changes were greater especially in the wavelength range of 480–650 nm. FIG. 10 shows the change in the absorption of nitrified myoglobin solution due to hydrogen sulphide at wavelength 580 nm.

It can be stated that the optical properties of myoglobin are changed by the action of hydrogen sulphide. This change is visible and it can be detected instrumentally. This change in the colour of myoglobin can be utilised for the indication of freshness and storage time of foodstuffs, preferably poultry products. For instance, in packages containing fresh chicken drumsticks, hydrogen sulphide concentrations as high as 0.6–1.1 mg/l were formed in the gas space during 21 days of storage at +5° C.

EXAMPLE 2

Indicators Prepared from Myoglobin and Agarose Gel

Small squares (size 11 mm×11 mm) cut from a sheet of agarose (2%, thickness 2–3 mm) were soaked with myoglobin (0.5–4.0 mg) dissolved in sodium phosphate buffer (40 mM, pH 6.8). The agarose squares were heat-sealed in polyethylene foil (thickness 50 $\mu$m). In some experiments, myoglobin reduced with sodium dithionite was used. The indicators were enclosed in airtight vessels and a known amount of gaseous hydrogen sulphide was added into the vessels. After 3–11 days of exposure of the indicators to hydrogen sulphide, the change in their colour was measured by means of a chromoscope (Minolta Chroma Meter) using L*a*b chromaticity coordinates. An index ($\Delta E$) describing the total colour change was calculated from formula (1).

$$\Delta E = (\Delta L^2 + \Delta a^2 + \Delta b^2)^{1/2} \quad (1)$$

Figure 11:
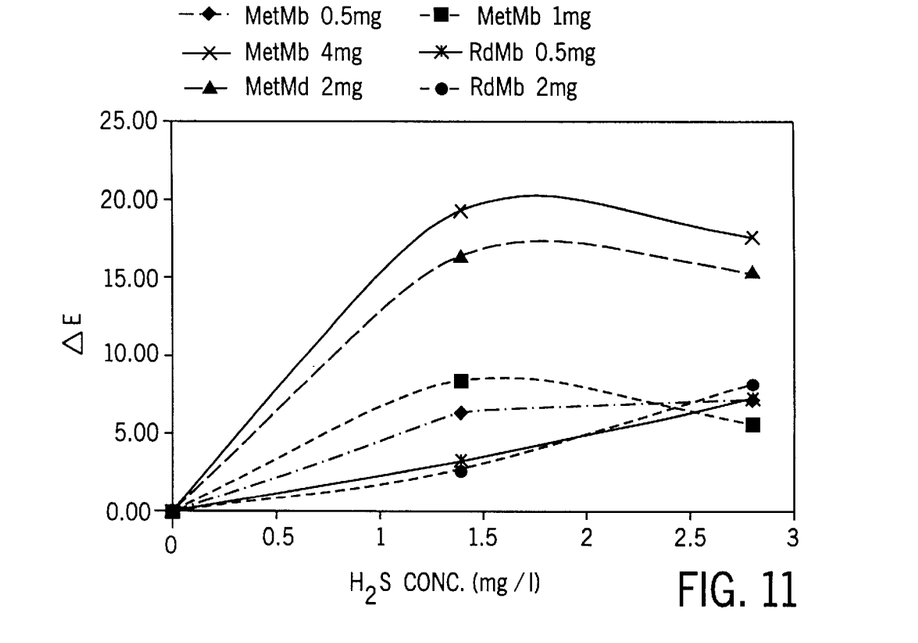
FIG. 11 presents the total index $\Delta E$ of colour change for hydrogen sulphide indicators (decay indicators) produced by absorbing myoglobin in agarose gel as compared with a blank sample ($[H_2O]=0$). MetMb=a commercial myoglobin mainly consisting of metmyoglobin, and RdMb=myoglobin reduced with sodium dithionite.

It could be seen that the colour of the indicators, had changed from brown to green and the colour change was the more pronounced the lower concentrations of myoglobin were used. FIG. 11 presents the colour change in these myoglobin based indicators immobilised in agarose, as a function of hydrogen sulphide concentration. The change has been calculated by comparing with a blank sample ($[H_2S]=0$).

EXAMPLE 3

Indicators Prepared from Myoglobin and Filter Paper

Figure 12:
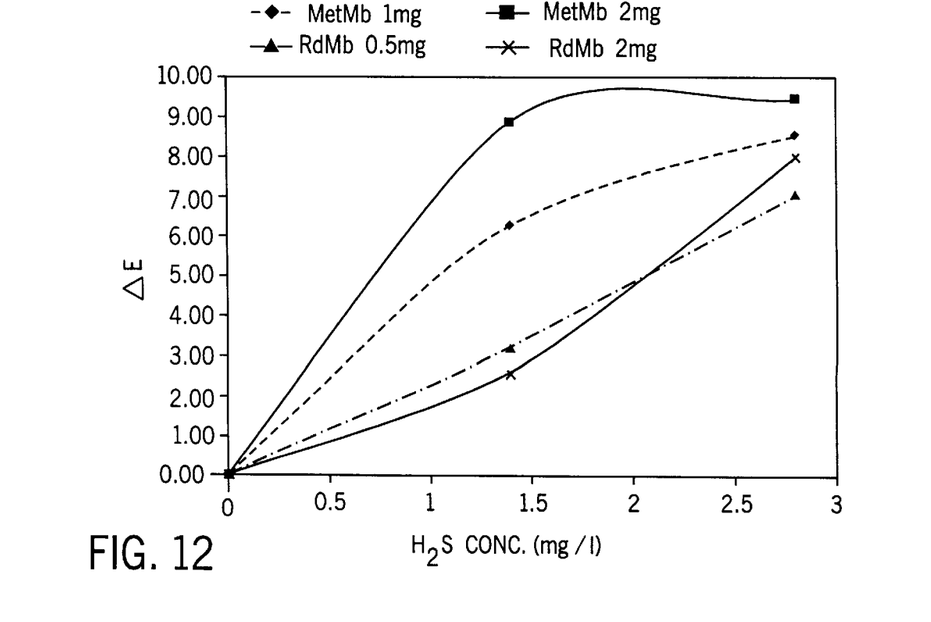
FIG. 12 presents the total index $\Delta E$ of colour change for hydrogen sulphide indicators (decay indicators) produced by absorpbing, as compared with a blank sample ($[H_2O]=0$)

Filter paper pieces (size 20 mm×20 mm, Whatman n:o 1) were soaked with myoglobin (0.5–2 mg) dissolved in sodium phosphate buffer (40 mM, pH 6.8). The indicators were prepared and the measurements carried out as in Example 2. Visual observation showed that the colour of the indicators had changed from brown to green and the colour change was the more pronounced the lower concentrations of myoglobin were used. FIG. 12 presents the total index of colour change for these myoglobin based indicators immobilised in filter paper as a function of hydrogen sulphide concentration. The change has been calculated by comparing with a blank sample ($[H_2S]=0$).

EXAMPLE 4

Oxidation Reaction Catalysed by Laccase

Figure 13:
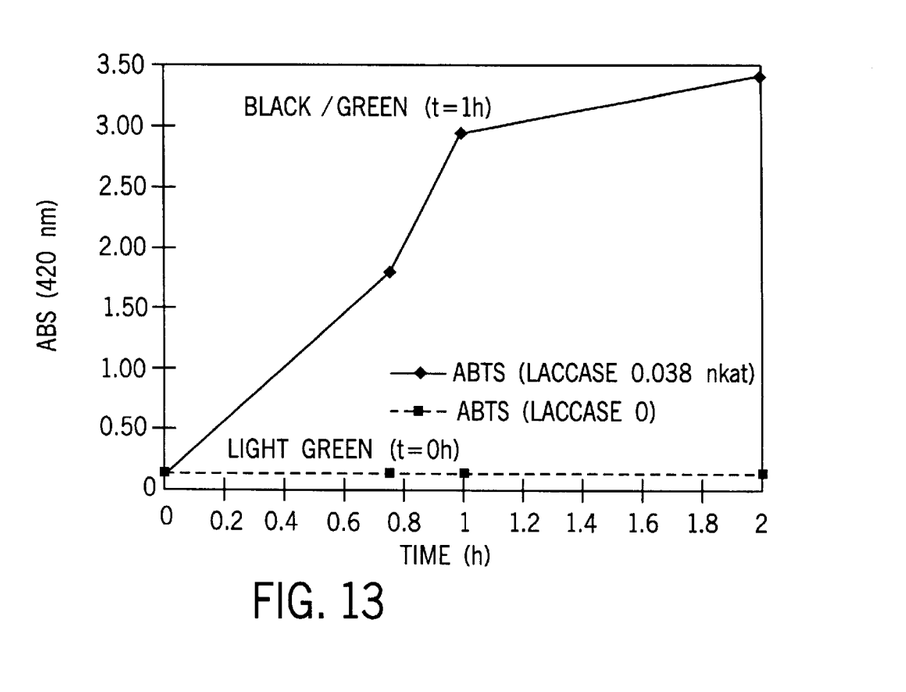
FIG. 13 represents the absorption of ABTS (420 nm) as a function of time in an oxidation reaction catalysed by laccase (0.038 nkat)
Figure 14:
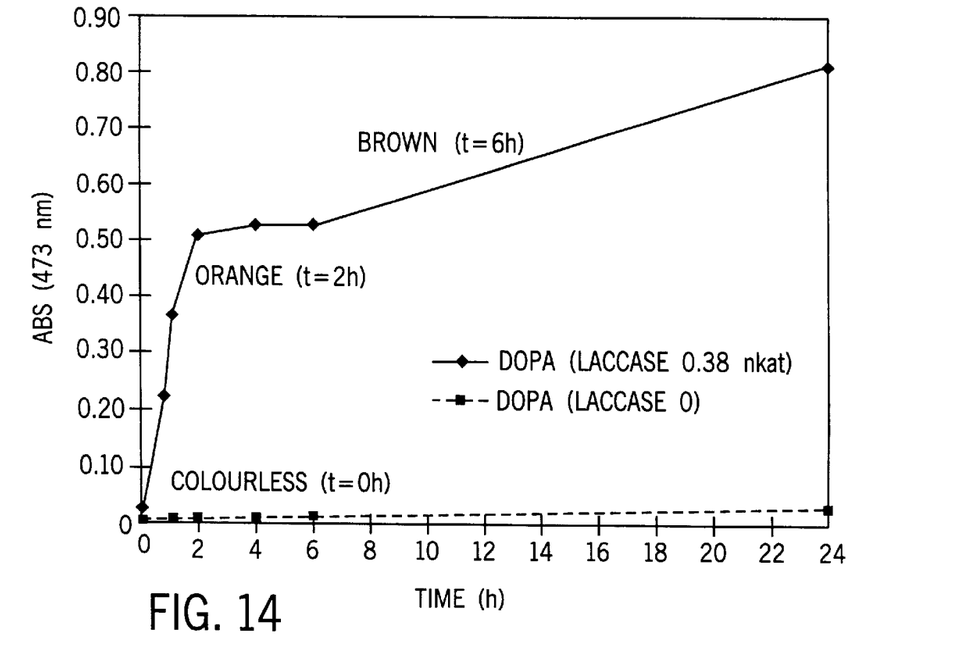
FIG. 14 represents the absorption of DOPA (473 nm) as a function of time in an oxidation reaction catalysed by laccase (0.38 nkat)

When polyphenoloxidases, preferably laccase, oxidise 2,2'-azino-di-ethylbenzothiazoline-6-sulfonate (ABTS) and DL-3,4-dihydroxyphenylalanine (DL-DOPA), the colour of the reaction products differs from the substrates. FIGS. 13 and 14 show the colour change in ABTS and DL-DOPA caused by laccase in the presence of oxygen as a function of time. The reaction was performed at room temperature and the concentration of ABTS and DOPA was 1.4 mM. In the oxidation reaction catalysed by laccase, the colour of ABTS changes from green to brown/grey and the colour of DOPA first changes to orange and subsequently to brown/grey. Thus, from both substrates an oxidation product readily discernible by visual observation is produced.

EXAMPLE 5

Laccase Based Oxygen Indicators 2,2'-azino-di-ethylbenzthiazoline-6-sulfonate (ABTS) was blended with low-melting agarose (4%) (2.5 mg/ml agarose). The indicators were prepared from pieces of sheet-like substrate cast from ABTS-agarose (thickness about 4 mm), which were treated with a laccase containing solution as in Example 2. The indicators thus prepared were stored in bags made from oxygen-tight laminate foil in conditions specified in table 1, which also shows the changes in the colour of the indicator that occurred during storage. The lower the storage temperature was and the less oxygen was present, the better was the colour of the indicators preserved unchanged before use. Thus, by adjusting the storage conditions it is possible to contribute towards preserving the colour of laccase based indicators unchanged before use.

TABLE 1

The effect of storage conditions on colour change in laccase based indicators during storage

| Storage conditions for laccase based indicators (temperature, method of oxygen removal) | Total index $\Delta E$ of colour change during storage (7 d) |
| --- | --- |
| +5° C., no oxygen removal | 21.6 |
| +5° C., oxygen removed by nitrogen flushing | 12.5 |
| +5° C., oxygen removed by nitrogen flushing and using an iron-acetic acid mixture | 9.5 |
| −20° C., no oxygen removal | 8.3 |

TABLE 1-continued

The effect of storage conditions on colour change
in laccase based indicators during storage

| Storage conditions for laccase based indicators (temperature, method of oxygen removal) | Total index ΔE of colour change during storage (7 d) |
|---|---|
| −20° C., oxygen removed by nitrogen flushing | 4.5 |
| +5° C., indicators prepared in oxygen-free conditions | 3.7 (storage time 6 d) |

EXAMPLE 6

Reaction of Laccase Based Indicator with Oxygen

Figure 15:
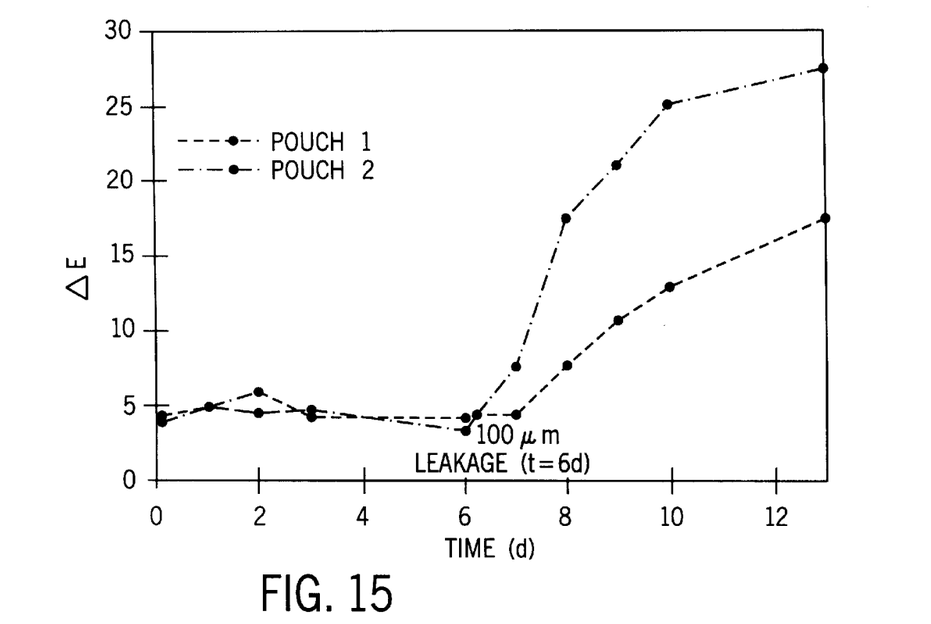
FIG. 15 illustrates the operation of oxygen indicators based on an ABTS-laccase system and enclosed in an oxygen-tight bag when used as leakage indicators.

Laccase based indicators were prepared in oxygen-free conditions according to example 5 and immediately enclosed in oxygen-tight laminate foil bags together with a low-capacity deoxidiser. When a perforation (100 μm in diameter) was mad in the bags, the colour of the indicators was clearly changed from very light green to green. The colour change was measured by means of a chromoscope and the total index ΔE of colour change was calculated. FIG. 15 shows the colour change ΔE in the laccase based indicators enclosed in oxygen-tight bags as a function of storage time. It can be stated that the laccase based indicators function as leakage indicators and the colour change can be perceived both visually and instrumentally.

EXAMPLE 7

Effect of Temperature on the Rate of Colour Change

Figure 16:
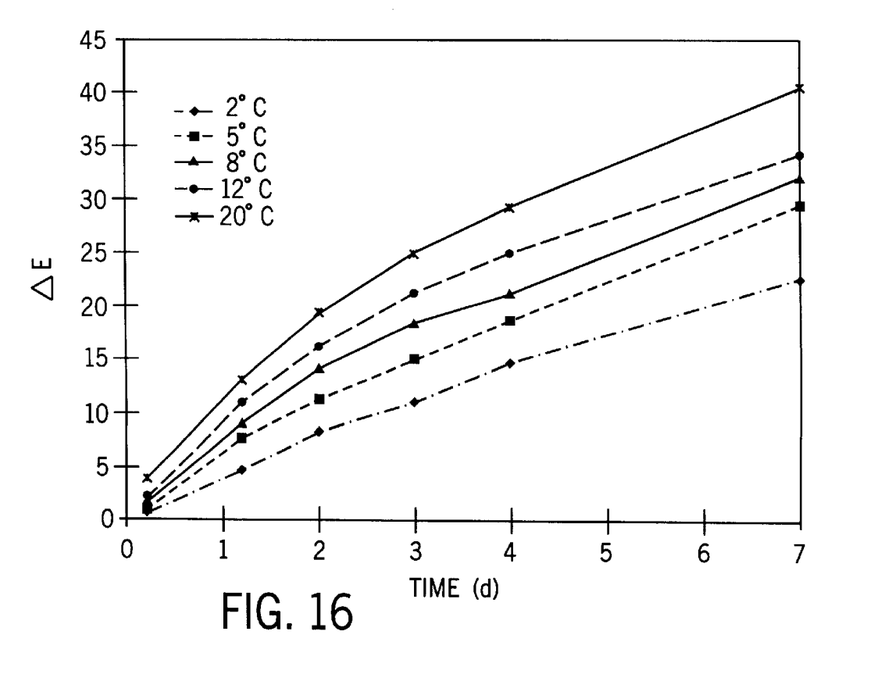
FIG. 16 represents the effect of temperature on the speed of colour change in an oxygen indicator based on laccase.

Squares (11 mm×11 m) of ABTS containing agarose were placed on a polyethylene foil on a Petri dish. Laccase solution was pipetted onto each square and the indicators were covered with small pieces of polyethylene foil. The indicators were not enclosed in polyethylene foil by heat-sealing in order to keep them more readily accessible to oxygen. The indicators were incubated at various temperatures and the colour of the indicators was monitored using a Minolta Chroma Meter as in example 2. FIG. 16 shows the colour of the indicators as a function of time at different temperatures. The rate of the colour change is clearly dependent on the storage temperature of the indicators.

EXAMPLE 8

Effect of Indicator Foil on the Rate of Colour Change

Figure 17:
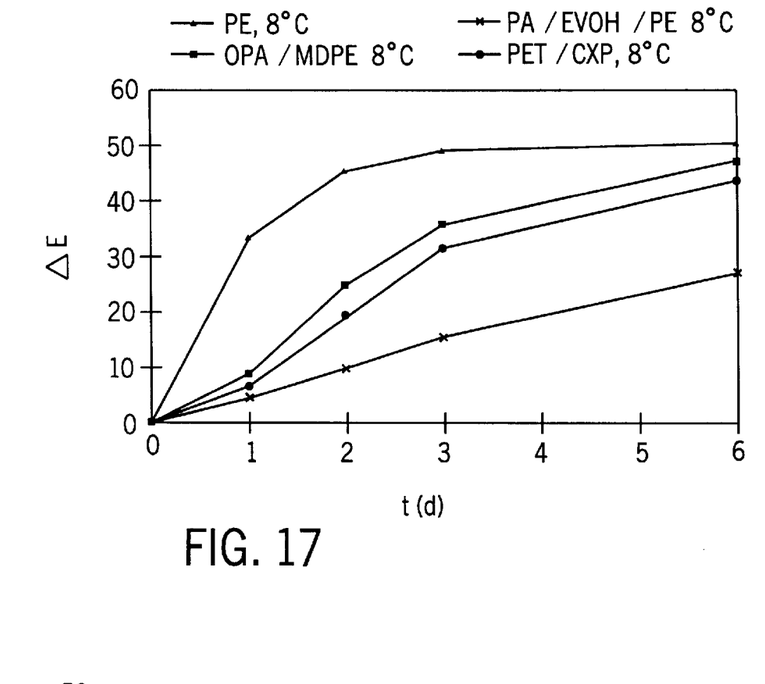
FIG. 17 represents the effect of an indicator foil on the speed of colour change in an oxygen indicator based on laccase.

Laccase based indicators were prepared in oxygen free conditions as in example 5 using different polymer laminates or polyethylene as indicator foil. The indicators were exposed to atmospheric oxygen at +8° C. FIG. 17 shows the colour of enzymatic oxygen indicators made of different laminates as a function of time. The foil used has a great importance regarding the rate of colour change. The sensitivity of the oxygen indicator can be adjusted by choosing an appropriate indicator foil.

EXAMPLE 9

Effect of Indicator Foil on Rate of Colour Change in Oxygen Indicator

Figure 18:
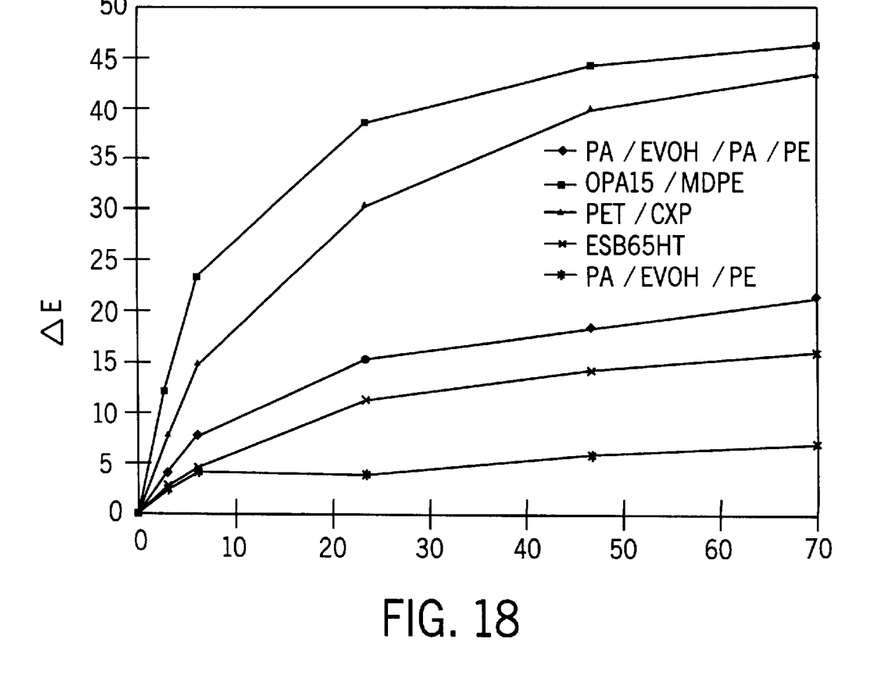
FIG. 18 represents the effect of an indicator foil on the speed of colour change in an oxygen indicator based on a chemical reagent sensitive to oxygen.

Oxygen sensitive chemical indicator mixture in powdery form was enclosed in bags made from different plastic laminates by heat-sealing. The indicators were exposed to atmospheric oxygen at +5° C. and 50% relative humidity. FIG. 18 shows the colour of the chemical indicators made from different laminates as a function of time. The foil used has a great importance regarding the rate of colour change. The sensitivity of the oxygen indicator can be adjusted by choosing an appropriate indicator foil.

EXAMPLE 10

Effect of Temperature on Oxygen Permeability of Polymer Foils

Figure 19A:
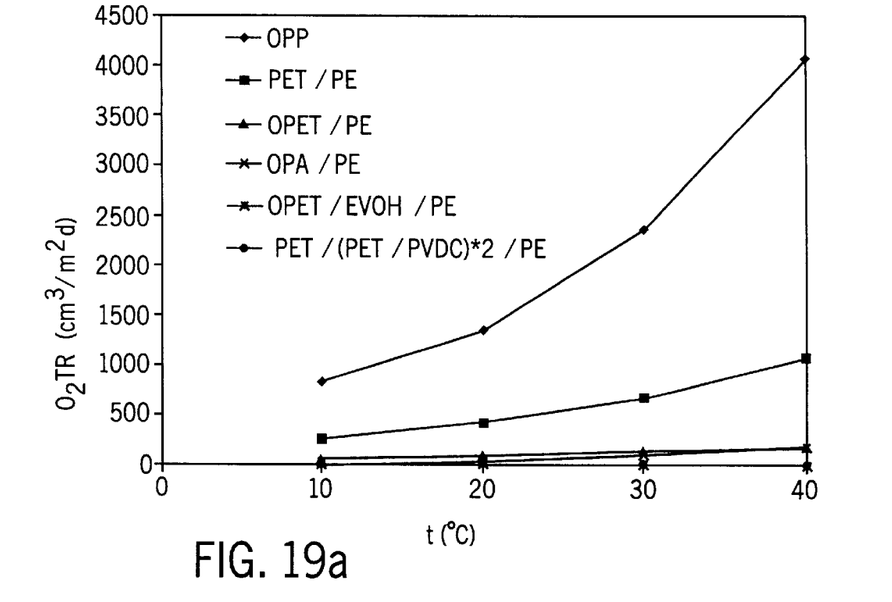
FIGS. 19a–c illustrate the effect of temperature on oxygen permeability of polymeric foils.
Figure 19B:
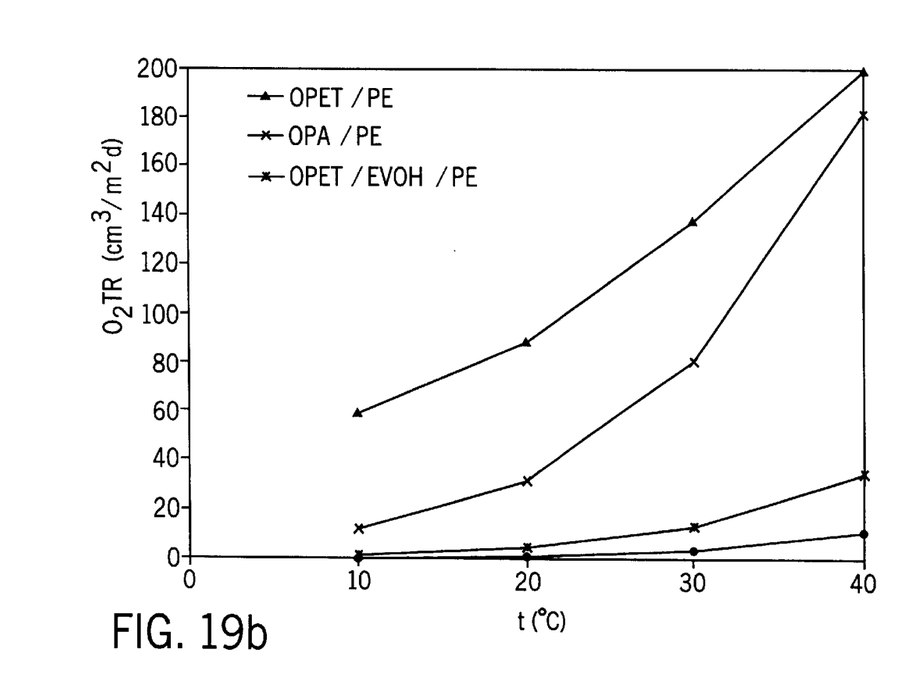
Figure 19C:
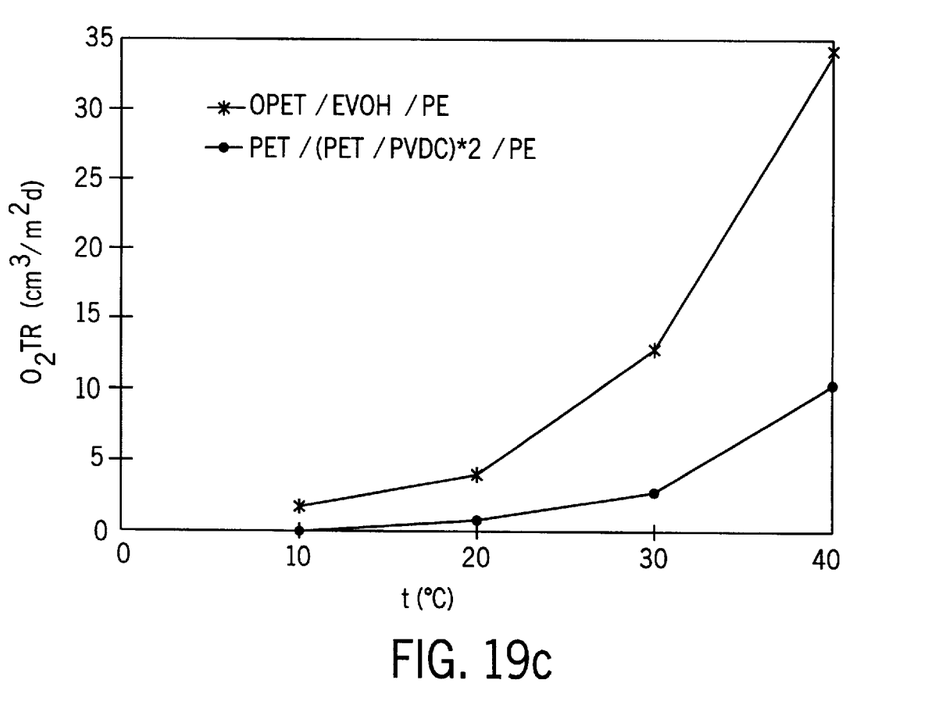

The oxygen permeability of different plastic laminates was measured at different temperatures using the Ox-Tran 2/20 MH apparatus, which is based on measuring the amount of oxygen that has penetrated the plastic foil. The relative humidity of the gases in the measurements was 60%. FIGS. 19a–c show the oxygen permeability of the foils used in the test, as a function of time. Oxygen permeability was exponentially dependent on the temperature, in such manner that the higher the oxygen permeability of the foil was, the slighter was the effect of temperature on the permeability. This phenomenon was apparent especially in the case of foils with a low oxygen permeability, a circumstance advantageous in respect of the operation of a leakage/time-temperature indicator. The strong temperature dependence of the permeability of the oxygen-tight foils enables their use as indicator components sensitive to storage temperature. On the other hand, the foils with a high oxygen permeability are much less dependent on temperature, which enables leakage detection independently of storage temperature.

The embodiment examples are intended to illustrate the invention without limiting it in any way.

What is claimed is:

1. A package (1) for decayable foodstuffs (2) comprising:
packaging material (3) forming a generally closed package space (4) for receiving a foodstuff, at least a portion of said packaging material being gas permeable; and
an indicator device for said package positioned on said package material,
said indicator device having;
an interior wall (10) and
an exterior wall (8), said exterior wall forming, with said interior wall, a generally closed indicator space outside said packaging material, said indicator space containing an indicator (6),
said exterior wall being exposed to an environment for the package and formed of a material (9) having a temperature dependent and controllable gas permeability to allow gas to pass through the exterior wall into said indicator space in a desired manner related to temperature and the length of environmental exposure time to which the package is subjected;
said interior wall (10) of said indicator device adjoining the package space (4), said interior wall being formed of a material controllable permeable to gas so that gas entering into and/or generated in the package space can penetrate from the package space into the indicator space in a desired manner;
said indicator (6) being responsive to the gas passing through said exterior wall from the environment for indicating the temperature and exposure time dependent ageing of the package, said indicator further being responsive to gas passing through said interior wall from said package space for indicating the presence of gas in the package space, whereby said indicator can simultaneously indicate package ageing, temperature dependent ageing, leakage occuring in said package space, and decay of foodstuffs in said package space.

an indicator device for said package positioned on said packaging material, said indicator device having;

an interior wall (8) and an exterior wall (10), said exterior wall forming, with said interior wall, a generally closed indicator space outside said packaging material, said indicator space containing an indicator (6), said exterior wall being exposed to an environment for the package and formed of a material (9) having a temperature dependent and controllable gas permeability to allow gas to pass through the exterior wall into said indicator space in a desired manner related to temperature and the length of environmental exposure time to which the package is subjected;

said interior wall (10) of said indicator device adjoining the package space (4), said interior wall being formed of a material controllable permeable to gas so that gas entering into and/or generated in the package space can penetrate from the package space into the indicator space in a desired manner;

said indicator (6) being responsive to the gas passing through said exterior wall from the environment for indicating the temperature and exposure time dependent ageing of the package, said indicator further being responsive to gas passing through said interior wall from said package space for indicating the presence of gas in the package space, whereby said indicator can simultaneously indicate package ageing, temperature dependent ageing, leakage occurring in said package space, and decay of foodstuffs in said package space.

2. A package as defined in claim 1 wherein said interior wall of said indicator device is further defined as permeable to a volatile factor indicating decay of foodstuff in said package space.

3. A package as defined in claim 1 wherein said exterior wall of said indicator device is laminated to said packaging material.

4. A package as defined in claim 1 wherein said indicator device is bonded to said packaging material.

5. A package as defined in claim 1 wherein said exterior wall of said indicator device is provided with a removable protector substantially impermeable to gas.

6. A package as defined in claim 1 wherein said indicator comprises at least a pair of indicator components having different response characteristics.

7. A package as defined in claim 1 wherein said interior wall of said indicator device is formed from a portion of said packaging material.

8. A package as defined in claim 7, wherein said interior wall of said indicator device is further defined as permeable to a volatile factor indicative of the decay of foodstuff in said package space, and wherein said indicator is responsive to said volatile factor for indicating foodstuff decay.

9. A package according to claim 1 wherein said indicator is responsive to a volatile compound produced by decay of the foodstuff in said package space.

10. A package as defined in claim 9 wherein said indicator is a myoglobin based indicator.

11. A package as defined in claim 1 wherein said indicator is further defined as an oxidation indicator.

12. A package as defined in claim 11 wherein said indicator employs an intermediate chemical reaction to provide an indication.

13. A package as defined in claim 12 wherein said indicator is based on changes in pH.

14. A package as defined in claim 12 wherein said indicator is based on a reaction employing a catalyst.

15. A package as defined in claim 14 wherein said catalyst is an enzyme.

16. A package as defined in claim 15 wherein said indicator is a laccase based indicator.

17. A package as defined in claim 1 wherein said interior wall of said indicator device is a separate element from said packaging material.

18. A package as defined in claim 17 wherein at least one of a permeable portion of said packaging material and said interior wall of said indicator device are provided with a removable protector substantially impermeable to gas.

19. A package as defined in claim 17 wherein a defined portion of said packaging material contains perforations and wherein said interior wall of said indicator device is placed on said perforated portion of said packaging material.

20. A package as defined in claim 19 wherein adhesive is interposed between said indicator device and said packaging material adjacent to said defined portion to attach said indicator device to said packaging material.

21. A package as defined in claim 17, wherein a defined portion of said packaging material is permeable to a volatile factor indicating the decay of foodstuff in said package space, wherein said interior wall of said indicator device is further defined as permeable to a volatile factor indicative of the decay of foodstuff in said package space, wherein said interior wall of said interior device is placed on said defined portion, and wherein said indicator is responsive to said volatile factor for indicating foodstuff decay.

22. A package as defined in claim 21 wherein the permeability of at least one of said packaging material and said interior wall is obtained by perforations.

23. A package as defined in claim 21 wherein adhesive is interposed between said indicator device and said packaging material adjacent to said defined portion to attach said indicator device to said packaging material.

* * * * *

UNITED STATES PATENT AND TRADEMARK OFFICE
CERTIFICATE OF CORRECTION

PATENT NO.    : 6,325,974 B1                                                      Page 1 of 1
DATED         : December 4, 2001
INVENTOR(S)   : Ahvenainen et al.

It is certified that error appears in the above-identified patent and that said Letters Patent is hereby corrected as shown below:

Title page,
Item [30], Foreign Application Priority Data, insert -- Jan. 22, 1997  (FI)  970267 --
Item [56], FOREIGN PATENT DOCUMENTS, insert
-- 627363      12/1994     EPO
484578         5/1992      EPO
93/15402       8/1993      WIPO --

Column 13,
Delete lines 7-40.

Column 14,
Line 47, delete "interior" in the second occurrence and substitute therefor -- indicator --

Signed and Sealed this

Twenty-fifth Day of February, 2003

JAMES E. ROGAN
*Director of the United States Patent and Trademark Office*